(12) United States Patent
Nishide et al.

(10) Patent No.: US 7,738,625 B2
(45) Date of Patent: Jun. 15, 2010

(54) X-RAY CT APPARATUS

(75) Inventors: Akihiko Nishide, Tokyo (JP); Kozaburo Fujimoto, Tokyo (JP); Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/394,754

(22) Filed: Feb. 27, 2009

(65) Prior Publication Data

US 2009/0220043 A1 Sep. 3, 2009

(51) Int. Cl.
*A61B 6/00* (2006.01)

(52) U.S. Cl. .......................... 378/19; 378/98.8

(58) Field of Classification Search ............... 378/19, 378/98.8, 109–112; 250/370.08, 370.09, 250/370.11
See application file for complete search history.

(56) References Cited

U.S. PATENT DOCUMENTS

| | | | |
|---|---|---|---|
| 3,699,340 A | 10/1972 | Hick et al. | |
| 4,529,882 A | 7/1985 | Lee | |
| 4,611,341 A | 9/1986 | Brody | |
| 4,963,746 A | 10/1990 | Morgan et al. | |
| 5,485,492 A | 1/1996 | Pelc | |
| 5,548,123 A | 8/1996 | Perez-Mendez et al. | |
| 6,052,433 A | 4/2000 | Chao | |
| 6,134,297 A | 10/2000 | Chao | |
| 6,922,462 B2 | 7/2005 | Acharya et al. | |
| 6,977,988 B2 * | 12/2005 | Niwa | 378/95 |
| 7,145,980 B2 | 12/2006 | Sakaguchi et al. | |
| 7,460,641 B2 * | 12/2008 | Niwa | 378/95 |
| 7,486,761 B2 | 2/2009 | Moore | |
| 2003/0223539 A1 | 12/2003 | Granfors et al. | |
| 2009/0046829 A1 | 2/2009 | Schweizer et al. | |

FOREIGN PATENT DOCUMENTS

JP 2004-065975 3/2004

* cited by examiner

*Primary Examiner*—Courtney Thomas
(74) *Attorney, Agent, or Firm*—Armstrong Teasdale LLP

(57) ABSTRACT

To provide an X-ray CT apparatus capable of acquiring information on energy of X-rays generated by an X-ray generating apparatus, an X-ray CT apparatus (100) comprises: an X-ray generating apparatus for generating X-rays and emitting the X-rays toward a subject; a first X-ray detector having a plurality of X-ray detection channels for detecting the X-rays emitted from the X-ray generating apparatus; a second X-ray detector for detecting the X-rays emitted from the X-ray generating apparatus in order to acquire information on energy of the X-rays emitted from the X-ray generating apparatus; and an X-ray energy information identifying section for identifying information on energy of the X-rays emitted from the X-ray generating apparatus based on the information detected by the second X-ray detector.

20 Claims, 5 Drawing Sheets

X-RAY CT APPARATUS

CROSS REFERENCE TO RELATED APPLICATIONS

This application claims the benefit of Japanese Patent Application No. 2008-049433 filed Feb. 29, 2008, which is hereby incorporated by reference in its entirety.

BACKGROUND OF THE INVENTION

The embodiments described herein relate to an X-ray CT (Computed Tomography) apparatus.

In general, an X-ray CT apparatus generates X-rays with a desired energy spectrum by controlling an X-ray tube voltage of an X-ray tube. There is also a known technique for obtaining a tomographic image based on CT values obtained using X-rays with an energy spectrum generated from an X-ray tube using a higher X-ray tube voltage and those obtained using X-rays with an energy spectrum generated from the X-ray tube using a lower X-ray tube voltage, as disclosed in Japanese Patent Application Laid Open No. 2004-065975, for example. More particularly, the technique includes a technique of obtaining a weighted subtraction image in which a certain material within a subject is enhanced using the fact that X-ray absorption coefficients of materials within the subject are different from one another in response to different energy spectra of X-rays. A technique of obtaining a CT image using projection data based on X-rays with two different energy spectra is sometimes referred to as dual energy imaging.

BRIEF DESCRIPTION OF THE INVENTION

Conventionally, energy of X-rays generated from an X-ray tube is identified by a specified X-ray tube voltage, and energy of actually generated X-rays cannot be accurately known. In recent years, it is desirable to accurately know energy of X-rays actually emitted by an X-ray tube in dual energy imaging as described above that rely upon the energy of X-rays.

Accordingly, embodiments of the present invention provide an X-ray CT apparatus capable of acquiring information on energy of X-rays generated by an X-ray generating apparatus.

An X-ray CT apparatus in a first aspect includes an X-ray generating apparatus for generating X-rays and emitting the X-rays toward a subject; a first X-ray detector having a plurality of X-ray detection channels for detecting the X-rays emitted from said X-ray generating apparatus; a second X-ray detector for detecting the X-rays emitted from said X-ray generating apparatus in order to acquire information on energy of the X-rays emitted from said X-ray generating apparatus; and an X-ray energy information identifying section for identifying information on energy of the X-rays emitted from said X-ray generating apparatus based on the information detected by said second X-ray detector.

An X-ray CT apparatus in a second aspect of the invention is the X-ray CT apparatus of the first aspect, wherein said second X-ray detector is disposed at an edge of said first X-ray detector.

An X-ray CT apparatus in a third aspect of the invention is the X-ray CT apparatus of the first or second aspect, wherein said second X-ray detector is a semiconductor detector capable of counting photons, and said information on energy is identified based on said count of photons.

An X-ray CT apparatus in a fourth aspect of the invention is the X-ray CT apparatus of the third aspect, wherein said semiconductor detector capable of counting photons is made by using a material selected from a group consisting of CdTe, CdZnTe, $HgI_2$, $PbI_2$ and GaAs.

An X-ray CT apparatus in a fifth aspect of the invention is the X-ray CT apparatus of the first or second aspect, wherein said second X-ray detector is an X-ray detector comprising scintillators and photodiodes and is provided thereabove with an X-ray filter, and said information on energy is identified based on X-rays passing through said X-ray filter.

An X-ray CT apparatus in a sixth aspect of the invention is the X-ray CT apparatus of any one of the first through fifth aspects, wherein said second X-ray detector is part of a plurality of X-ray detection channels of said first X-ray detector.

An X-ray CT apparatus in a seventh aspect of the invention is the X-ray CT apparatus of any one of the first through fifth aspects, wherein said first X-ray detector is an X-ray detector comprising scintillators and photodiodes.

An X-ray CT apparatus in an eighth aspect of the invention is the X-ray CT apparatus of any one of the first through seventh aspects, wherein said second X-ray detector comprises a plurality of X-ray detection channels.

An X-ray CT apparatus in a ninth aspect of the invention is the X-ray CT apparatus of the eighth aspect, wherein said plurality of X-ray detection channels are arranged in a body axis direction of said subject.

An X-ray CT apparatus in a tenth aspect of the invention is the X-ray CT apparatus of the first aspect, wherein said second X-ray detector is disposed in proximity of said X-ray generating apparatus.

An X-ray CT apparatus in an eleventh aspect of the invention is the X-ray CT apparatus of the tenth aspect, wherein said second X-ray detector is a semiconductor detector capable of counting photons, and said information on energy is identified based on said count of photons.

An X-ray CT apparatus in a twelfth aspect of the invention is the X-ray CT apparatus of the eleventh aspect, wherein said semiconductor detector capable of counting photons is made by using a material selected from a group consisting of CdTe, CdZnTe, $HgI_2$, $PbI_2$ and GaAs.

An X-ray CT apparatus in a thirteenth aspect of the invention is the X-ray CT apparatus of the tenth aspect, wherein said second X-ray detector is an X-ray detector comprising scintillators and photodiodes and is provided thereabove with an X-ray filter, and said information on energy is identified based on X-rays passing through said X-ray filter.

An X-ray CT apparatus in a fourteenth aspect of the invention is the X-ray CT apparatus of any one of the first through thirteenth aspects, wherein said X-ray generating apparatus generates X-rays with a plurality of energy spectra based on a plurality of X-ray tube voltages.

An X-ray CT apparatus in a fifteenth aspect of the invention is the X-ray CT apparatus of the fourteenth aspect, wherein said X-ray generating apparatus generates said X-rays with a plurality of energy spectra by a single X-ray generating apparatus switching between a plurality of X-ray tube voltages on a view-by-view or views-by-views basis.

An X-ray CT apparatus in a sixteenth aspect of the invention is the X-ray CT apparatus of any one of the first through fifteenth aspects, further comprising: a data correcting section for correcting data based on X-rays detected by said first X-ray detector, the correction being made based on the information on energy identified by said X-ray energy information identifying section.

An X-ray CT apparatus in a seventeenth aspect of the invention is the X-ray CT apparatus of any one of the first through sixteenth aspects, further comprising: a display section for displaying the information on energy of the X-rays emitted from said X-ray generating apparatus.

According to the embodiments described herein, an X-ray CT apparatus is provided that is capable of acquiring information on energy of X-rays generated by an X-ray generating apparatus by making the X-ray CT apparatus comprise a second X-ray detector for detecting X-rays emitted from the X-ray generating apparatus and have an X-ray energy information acquiring section for acquiring information on energy of X-rays detected by the second X-ray detector.

DETAILED DESCRIPTION OF THE INVENTION

Figure 1:
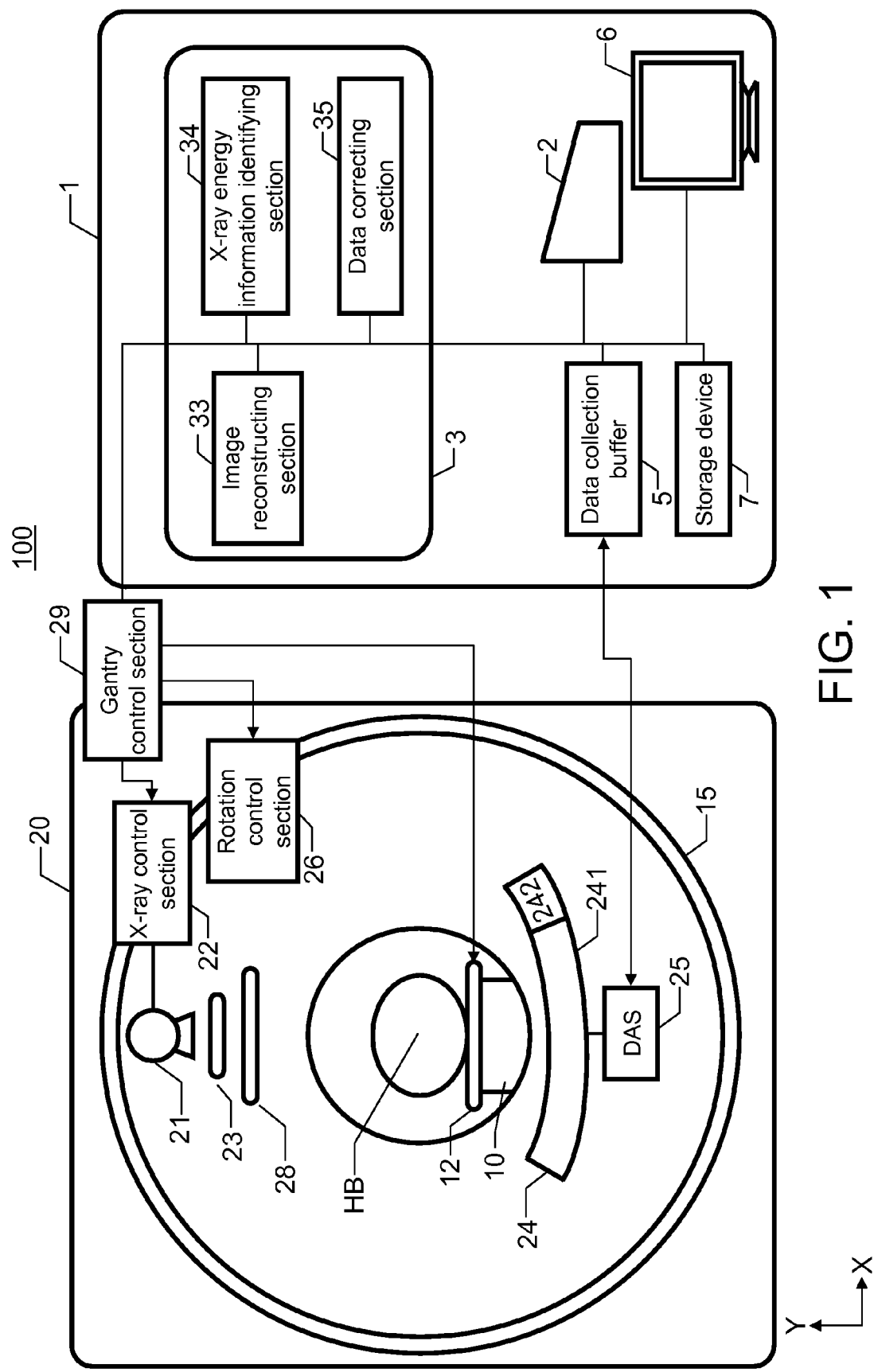
FIG. 1 is a block diagram showing an exemplary X-ray CT apparatus.

FIG. 1 is a block diagram of a configuration of an exemplary X-ray CT apparatus 100. The X-ray CT apparatus 100 comprises an operator console 1, an imaging table 10, and a scan gantry 20.

The operator console 1 comprises an input device 2 for accepting an input from a human operator, such as a keyboard or a mouse, a central processing apparatus 3 for executing pre-processing, image reconstruction processing, post-processing, etc., a data collection buffer 5 for collecting X-ray detector data collected at the scan gantry 20. The operator console 1 also comprises a monitor 6 for displaying a tomographic image image-reconstructed from projection data obtained by pre-processing the X-ray detector data, and a storage device 7 for storing programs, the X-ray detector data, projection data, and X-ray tomographic images. Imaging conditions are input via the input device 2 and stored in the storage device 7. The imaging table 10 comprises a cradle 12 for laying thereon a subject HB to be carried into/out of a bore of the scan gantry 20. The cradle 12 is vertically and horizontally moved/translated by a motor incorporated in the imaging table 10.

The scan gantry 20 comprises an X-ray tube 21, an X-ray control section 22, a collimator 23, a beamforming X-ray filter 28, a multi-row X-ray detector 24, a data collecting apparatus 25 (DAS: Data Acquisition System) 25. The X-ray control section 22 switches the tube voltage of the X-ray tube 21 between 80 kV and 140 kV. The data collecting apparatus 25 converts analog signals from the multi-row X-ray detector 24 into digital signals over a predefined integration time.

The multi-row X-ray detector 24 is provided with a first X-ray detector 241 having a plurality of X-ray detection channels for detecting X-ray projection data of the subject and a second X-ray detector 242 for acquiring information on energy of emitted X-rays.

The scan gantry 20 further comprises a rotation control section 26 for controlling rotation of the rotating section 15 having the X-ray tube 21 that rotates around a body axis of the subject HB, and a gantry control section 29 for communicating control signals or the like with the operator console 1 and imaging table 10. The beamforming X-ray filter 28 is provided for reducing subject exposure to radiation, and it is an X-ray filter configured to have a thickness that is smallest in a direction of X-rays traveling toward a center of rotation, which is an imaging center, and becomes larger toward peripheries to absorb more X-rays.

The central processing apparatus 3 has an image reconstructing section 33, an X-ray energy information identifying section 34, and a data correcting section 35.

The image processing section 33 executes pre-processing, beam hardening correction processing, image reconstruction processing, post-processing, dual energy image reconstruction processing, etc.

The pre-processing includes offset correction, logarithmic transform processing, X-ray dose correction, and sensitivity correction.

The beam hardening correction processing executes processing of beam hardening correction on projection data. Beam hardening refers to a phenomenon that an X-ray energy distribution of continuous X-rays varies as such X-rays travel inside a material, resulting in variation in CT values (brightness) in a cross section. The beam hardening correction is applied to projection data in a slice direction and a channel direction.

The image reconstruction processing involves receiving pre-processed projection data and reconstructing an image based on the projection data. The projection data is subjected to fast Fourier transform (FFT) for transforming the data into that in a frequency domain, and the resulting data is convolved with a reconstruction function Kernel(j) in a spatial domain and subjected to inverse Fourier transformation. The image reconstructing section 34 then applies three-dimensional backprojection processing to the projection data convolved with the reconstruction function Kernel(j), and thereafter, applies post-processing to the data to convert it into a tomographic image having CT values on a pixel-by-pixel basis, which tomographic image is obtained in each cross section (xy plane) along a body axis direction of the subject HB (Z-axis direction). The image reconstructing section 34 stores these tomographic images in the storage device 7.

The dual energy image reconstruction processing involves image-reconstructing a two-dimensional distribution tomographic image of X-ray tube voltage dependent information relating to a distribution of a certain material (atoms), which image is sometimes called a tomographic image by dual energy imaging, from X-ray projection data obtained using a lower X-ray tube voltage kV1 and that obtained using a higher X-ray tube voltage kV2. The tomographic images in dual energy imaging that can be obtained include so-called water-equivalent image, fat-equivalent image, contrast-equivalent image, bone-equivalent image or the like, in which water, fat, contrast agent, bone or the like is substantially eliminated, respectively.

The X-ray energy information identifying section 34 uses data based on a result detected by the second X-ray detector 242 to calculate or estimate energy information and identify it.

The data correcting section 35 corrects data based on X-rays detected by the first X-ray detector 241 based on the energy information identified by the X-ray energy information identifying section 34.

Next, acquisition of X-ray energy information by the second X-ray detector 242 and identification of X-ray energy by the X-ray energy information identifying section 34 using the aforementioned X-ray CT apparatus 100 will be described in detail with reference to embodiments.

Embodiment 1 shows an example employing a so-called photon-counting X-ray detector, which is a semiconductor detector capable of counting photons, as the second X-ray detector 242.

Figure 2:
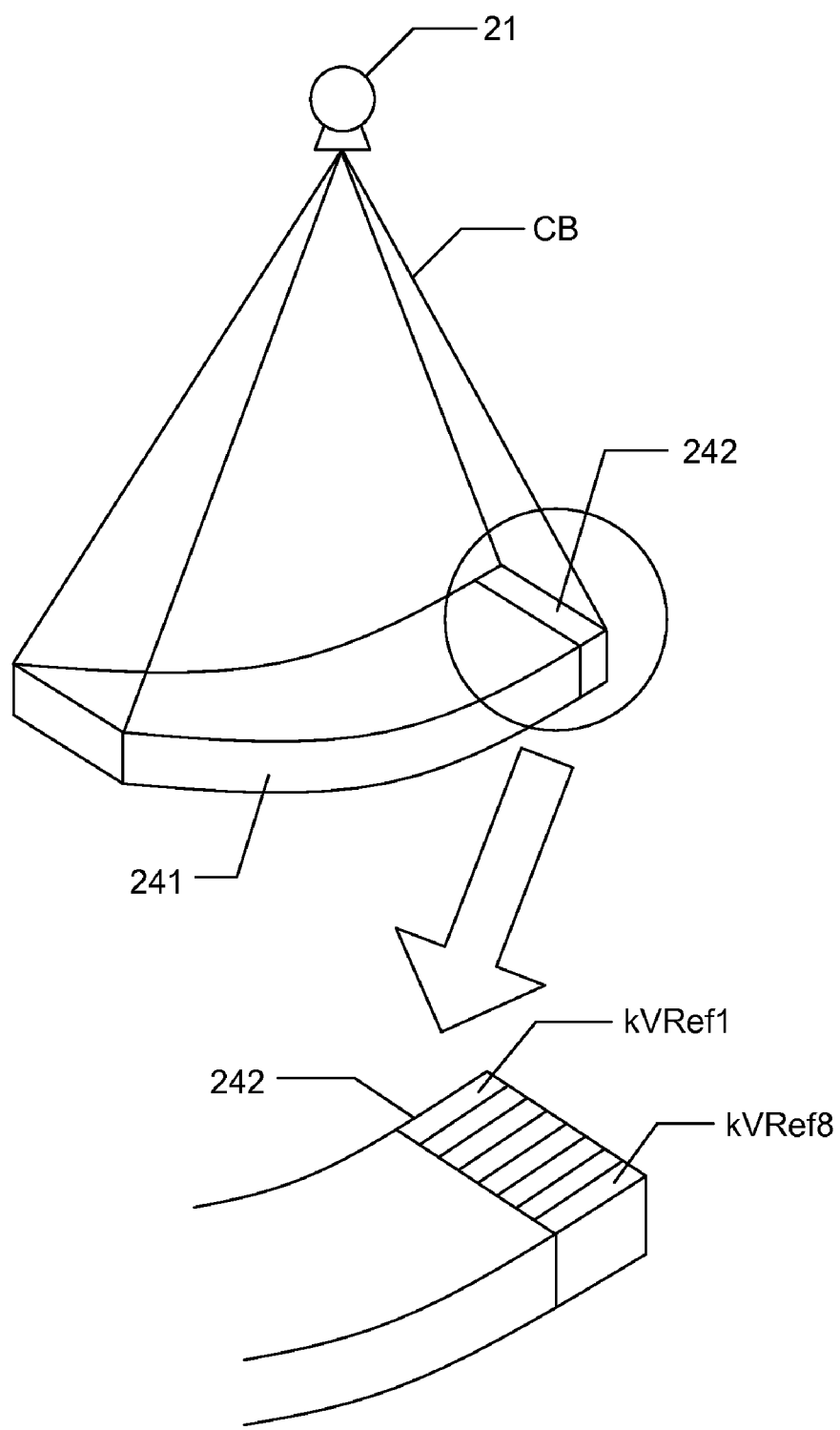
FIG. 2 is a diagram for explaining an exemplary second X-ray detector that may be used with the X-ray CT apparatus shown in FIG. 1.

FIG. 2 is a diagram showing a disposition of a second X-ray detector according to the present embodiment. In the drawing, the second X-ray detector 242 constructed from a photon-counting X-ray detector in which a material directly reactive with X-ray photons such as a CdTe semiconductor is employed as a detector element material is disposed adjacent to an edge of the first X-ray detector 241 in a rotation direction (channel direction), which detector 241 is a so-called scintillating X-ray detector constructed from a combination of scintillators and photodiodes. In the present embodiment, it is assumed that the second X-ray detector 242 has eight X-ray detection channels (kVRef1-kVRef8). Moreover, the second X-ray detector 242 may be disposed at any other position than the edge of the first X-ray detector 241 in the rotation direction (channel direction), insofar as its channels lie at a position unlikely to be obstructed by the subject. In this case, X-rays having a similar solid angle and similar quality to those of the first X-ray detector for detecting X-rays in the imaging region can be captured by the second X-ray detector 242. Specifically, since the emitted X-rays equally pass through the X-ray filter near the X-ray tube 21 and beamforming X-ray filter 28, thereby forming a cone beam CB, they have similar X-ray quality for the detectors 241 and 242. Moreover, since the length from the X-ray focal spot is insignificantly different in geometry, the X-rays have a similar signal level for the detectors 241 and 242.

As X-rays emitted using the X-ray CT apparatus 100 impinge upon the first X-ray detector 241 for each view, they also impinge upon the channels kVRef1-kVRef8 of the second X-ray detector 242, and a signal is counted for each channel based on an electrical charge generated at a semiconductor element depending upon energy of X-ray photons. At that time, a threshold(s) for energy may be defined to count separately for energy ranges. From a result of the count, the X-ray energy information identifying section 34 determines energy information at those channels based on a calculation method defined as appropriate for likely-to-be-optimal energy (for example, an energy range containing a peak of the count, or an average of a plurality of energy ranges containing a peak of the count), and identifies energy information in a current view based on a calculation method defined as appropriate for optimal energy information based on the energy information for the eight channels (for example, an average of eight pieces of energy information).

For example, when X-rays are emitted while switching the X-ray tube voltage between 80 kV and 140 kV on a view-by-view or views-by-views basis in dual energy imaging, thresholds that divide photon energy into three ranges, 80 kV, 140 kV and middle kV, are provided, and energy information representing 80 kV, 140 kV or middle kV is acquired for every view(s). As a result, one can know whether X-ray projection data is under 80 kV, 140 kV, or transient kV during switching of the X-ray tube voltage, for each view.

It should be noted that in the aforementioned embodiment, a semiconductor material employed in the photon-counting X-ray detector is not limited to CdTe, and CdZnTe, $HgI_2$, $PbI_2$, GaAs, etc. may be employed.

Moreover, while the present invention is achieved in the embodiment above by employing a most widespread scintillating X-ray detector for the first X-ray detector and adding the second X-ray detector to the conventional multi-row X-ray detector, the photon-counting X-ray detector may be employed for the first X-ray detector, that is, partial channels in the photon-counting X-ray detector may be served as the second X-ray detector.

Furthermore, some scintillating X-ray detectors have X-ray dose correction channel(s), in which case the second X-ray detector of the present embodiment may be disposed adjacent to such X-ray dose correction channel(s).

Additionally, while energy information with higher accuracy may be obtained by employing more X-ray detector elements for the second X-ray detector in the embodiment above, the X-ray detector elements are not limited to provision in a plural number, and one or more X-ray detector elements may be provided.

Embodiment 2 shows an example in which outermost channels of the multi-row X-ray detector 24 in the rotation direction is used for the second X-ray detector 242. That is, the second X-ray detector is constructed from a scintillating X-ray detector in Embodiment 2.

Figure 3:
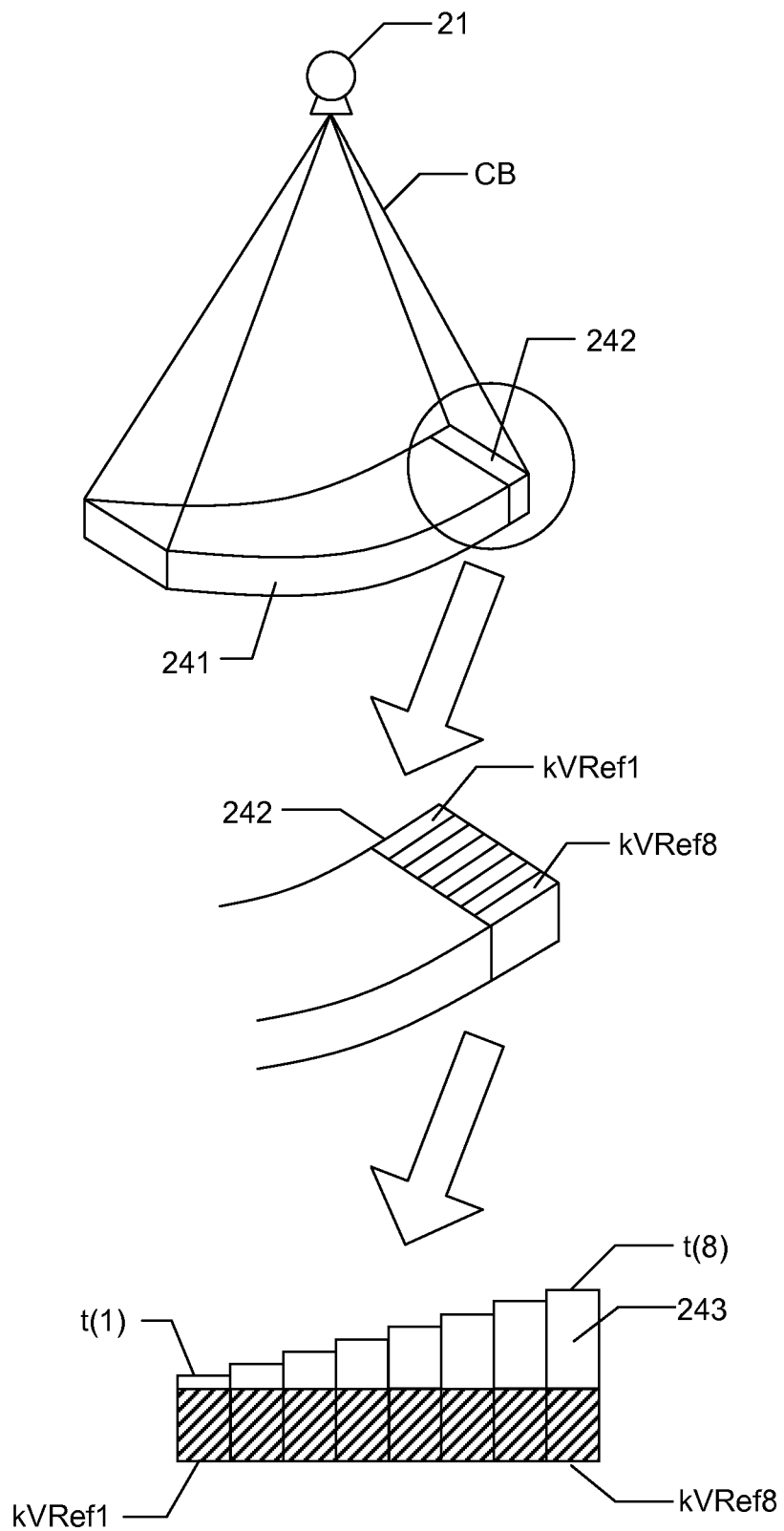
FIG. 3 is a diagram for explaining another exemplary second X-ray detector that may be used with the X-ray CT apparatus shown in FIG. 1.

FIG. 3 is a diagram showing a disposition of a second X-ray detector according to the present embodiment. In the drawing, there is shown an example in which eight energy acquisition channels (kVRef1-kVRef8) constituting the second X-ray detector 242 are provided. It should be noted that in the present embodiment, similarly to Embodiment 1, the second X-ray detector 242 may not necessarily be outermost channels of the multi-row X-ray detector 24 in the rotation direction (channel direction), insofar as its channels lie at a position unlikely to be obstructed by the subject. Moreover, in the present embodiment, similarly to Embodiment 1, X-rays similar to those at the first X-ray detector can be captured at the second X-ray detector 242.

Furthermore, some scintillating X-ray detectors have X-ray dose correcting channel(s), in which case the second X-ray detector may be disposed adjacent to such X-ray dose detecting channel(s) and/or it may be served as the X-ray dose detecting channel(s) as well. Moreover, the second detector may be disposed in proximity of or adjacent to the multi-row X-ray detector 24 as a detector separate from the multi-row X-ray detector 24, rather than as the outermost channels of the multi-row X-ray detector 24 in the rotation direction.

Furthermore, as shown in FIG. 3, the second X-ray detector 242 is provided above its energy acquisition channels with an X-ray filter 243 having a varying thickness. The X-ray filter is assumed to have thicknesses t(1)-t(8). The X-ray filter 243 having a varying thickness causes X-rays with different energy wavelength bands to be input to the energy acquisition channels kVRef1-kVRef8.

Figure 4A:
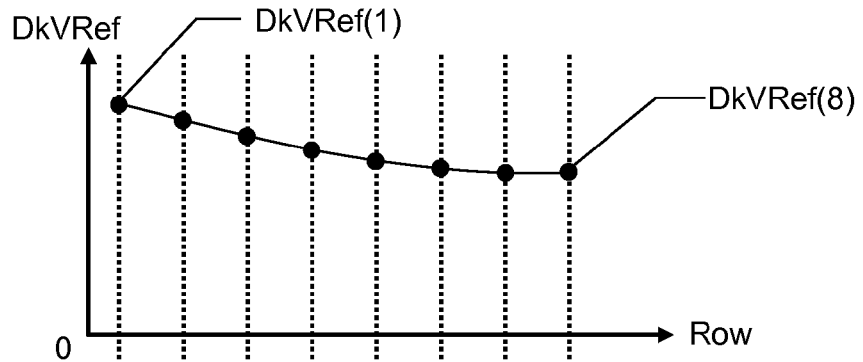
FIGS. 4A, 4B, and 4C are diagrams for explaining identification of energy information.
Figure 4B:
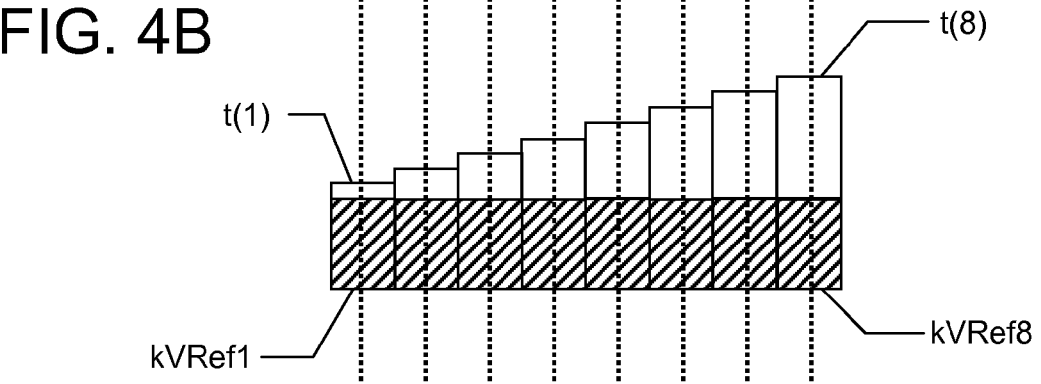
Figure 4C:
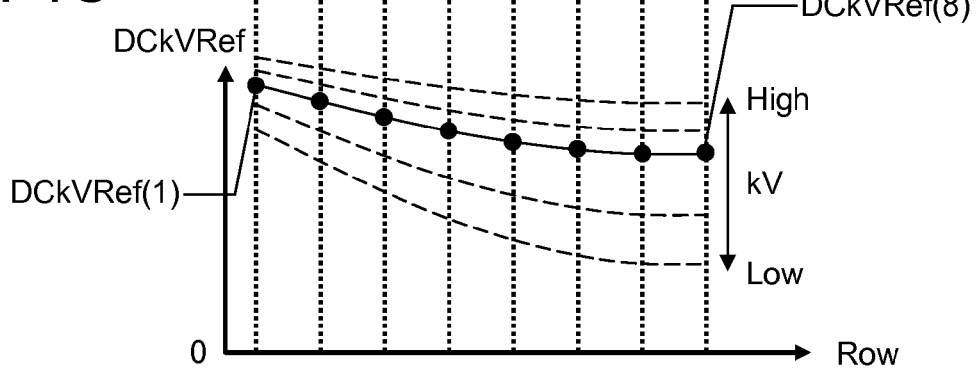

FIG. 4A shows outputs DkVRef(1)-DkVRef(8) of the energy acquisition channels kVRef1-kVRef8 when X-rays based on an X-ray tube voltage are input to the energy acquisition channels kVRef1-kVRef8 shown in FIG. 4B. FIG. 4C shows outputs DCkVRef(1)-DCkVRef(8) after the outputs DkVRef(1)-DkVRef(8) are corrected for attenuation by the thickness of the X-ray filter 243. The outputs DCkVRef(1)-DCkVRef(8) after attenuation by the thickness of the X-ray filter is corrected can be determined according to EQ. 1 below, where an output of an energy acquisition channel is represented as DkVRef(i), i=1-8, the thickness of the X-ray filter 242 is represented as t(i), an X-ray linear absorption coefficient of the material of the X-ray filter 242 is represented as p, and an output after X-ray filter thickness correction is represented as DCkVRef(i):

$$DCkVRef(i) = DkVRef(i) \cdot e^{\rho t(i)} \qquad \text{EQ. 1}$$

Although the output after the X-ray filter thickness correction is ideally equivalent to that of X-rays not passing through the filter, it exhibits variation due to energy of X-rays in practice. In the present embodiment, the variation in the output due to a difference in energy is actively used. Specifically, the X-ray energy information identifying section 34 stores therein a reference output after X-ray filter thickness correction (a solid dotted line in the graph of FIG. 4C for each level of energy beforehand, compares actual output energy with the reference, and identifies the measured output energy as information on energy of X-rays by calculation or estimation. For example, an average of the measured output energy may be served as energy information for a current view by calculation or estimation on a channel-by-channel basis.

Moreover, while energy information with higher accuracy may be obtained by employing more X-ray detector elements for the second X-ray detector in the embodiment above, the X-ray detector elements are not limited to provision in a plural number, and one or more X-ray detector elements may be provided.

Next, an example in which a second X-ray detector similar to that in Embodiment 1 or 2 is disposed in proximity of the X-ray tube 21 will be described as a variation.

Figure 5:
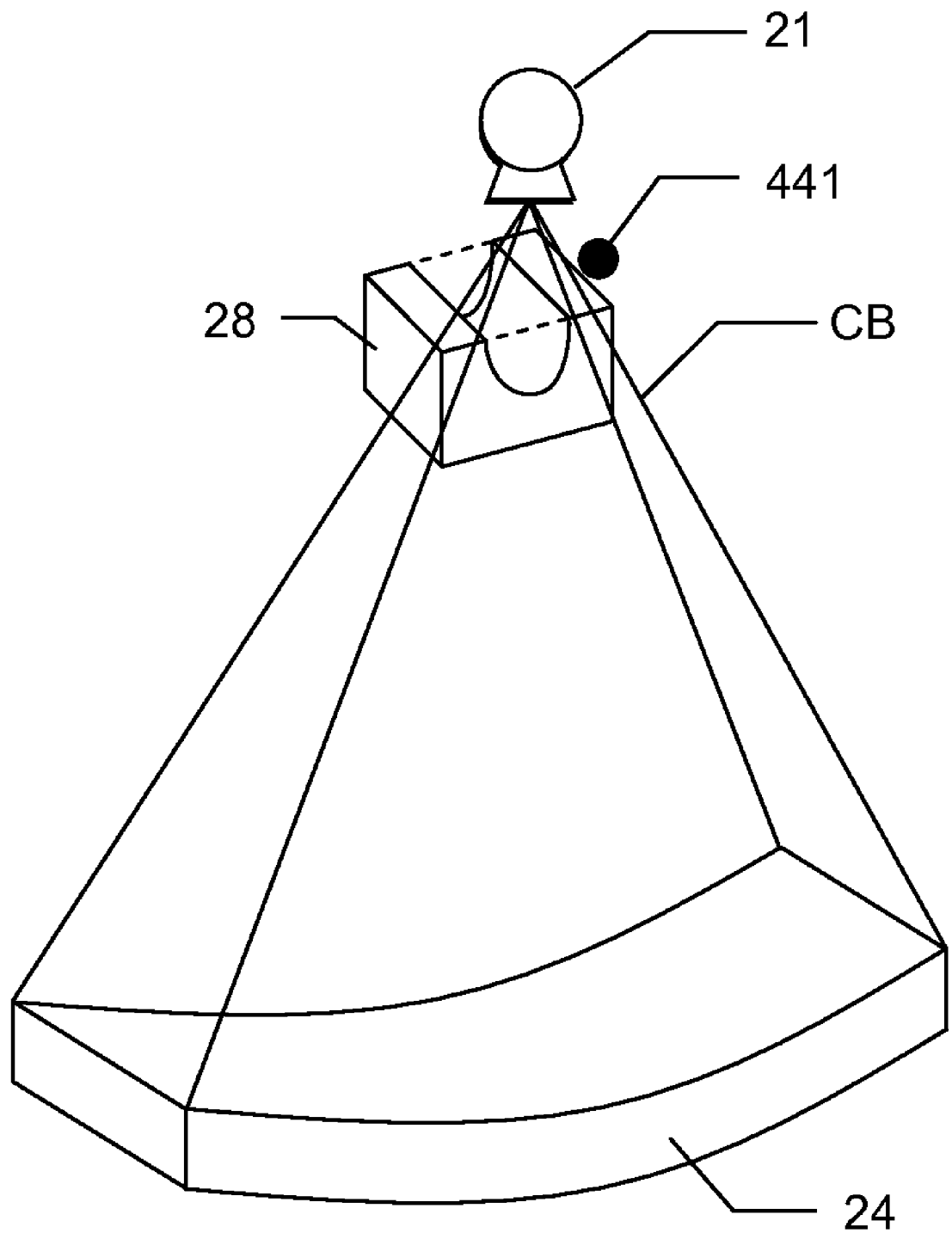
FIG. 5 is a diagram for explaining use of a second X-ray detector with the X-ray CT apparatus shown in FIG. 1.

FIG. 5 is a diagram showing a disposition of a second X-ray detector. In FIG. 5, a second X-ray detector 441 is disposed in proximity of the X-ray tube 21. Such a second X-ray detector 441 is not obstructed by a subject even if the subject is large-sized. In this case, X-rays input to the second X-ray detector 441 and those input to the multi-row X-ray detector 24 through the beamforming filter have different quality, and therefore, it is preferable to dispose an X-ray filter equivalent to the beamforming filter above the second X-ray detector, in addition to an X-ray filter similar to the aforementioned X-ray filter 242. It should be noted that acquisition of information on energy of X-rays may be achieved in this variation in a similar manner to that in Embodiment 1 or 2.

It should be noted that the information on energy of X-rays acquired in all embodiments above may be appended to X-ray projection data on, for example, a view-by-view basis.

Moreover, the information on energy of X-rays acquired in all embodiments above may be continuously displayed on the monitor 6 during a scan for monitoring the energy information.

Furthermore, the information on energy of X-rays acquired in all embodiments above may be used in data correction applied in the data correcting section 35 for obtaining a tomographic image. For example, when correction on X-ray projection data, such as beam hardening correction, executed at the image processing section 33 employs a function of the X-ray tube voltage (energy of X-rays), the correction may be performed using the acquired energy information based on the second X-ray detector in such a function. Alternatively, in a case that after correction using a function with a predefined X-ray tube voltage (energy of X-rays) has been performed, the X-ray energy information used in the correction is different from the energy information acquired based on the second X-ray detector, the X-ray projection data after the correction may be additionally subjected to correction that provides data as if the energy information acquired based on the second X-ray detector were used in the correction.

Moreover, another example of data correction may involve converting data of a subject acquired using X-rays with a certain energy spectrum into data acquired using X-rays with a different energy spectrum (which will be referred to as X-ray energy correction hereinbelow). In particular, one example of such correction may involve converting projection data under an X-ray tube voltage of 80 kV and that under an X-ray tube voltage of 140 kV acquired by dual energy imaging into projection data corresponding to an X-ray tube voltage of 120 kV.

It can be considered that the X-ray energy correction may be employed in optimizing noise by changing the X-ray tube voltage kV according to variation in composition or shape of the subject, for example, in a view direction or in a body axis direction, along with or instead of a change in X-ray tube current known in the art.

The X-ray energy correction may be achieved by several methods. In one embodiment, a scout scan is performed using the dual energy imaging technique to acquire information on composition of the subject. An X-ray absorption coefficient that depends upon composition and energy is applied to an image obtained by imaging using an arbitrary X-ray tube voltage, and the image is converted into data corresponding to a desired X-ray tube voltage for each component of the subject. In another embodiment, a weighted subtraction image obtained by performing dual energy imaging is converted for each component of the subject into data corresponding to a desired X-ray tube voltage based on an X-ray absorption coefficient that depends upon composition and energy.

Then, by applying the energy information identified as described above to such X-ray energy correction, accurate X-ray energy correction can be achieved.

It should be noted that the dual energy imaging technique in the embodiments above may be achieved by several methods. In one embodiment, a method includes switching the X-ray tube voltage of a single X-ray tube on a rotation-by-rotation basis to generate X-rays with the plurality of energy distributions as described earlier. In another embodiment, a method includes switching the X-ray tube voltage of a single X-ray tube on a view-by-view or views-by-views basis to generate X-rays with the plurality of energy distribution as described earlier. In yet another embodiment, a method includes using a plurality of X-ray tubes having different X-ray tube voltages to generate X-rays with the plurality of energy distributions as described earlier.

What is claimed is:

1. An X-ray Computed Tomography (CT) apparatus comprising:
    an X-ray generating apparatus configured to generate X-rays and to emit the X-rays toward a subject;
    a first X-ray detector comprising a plurality of X-ray detection channels configured to detect the X-rays emitted from said X-ray generating apparatus;
    a second X-ray detector configured to detect the X-rays emitted from said X-ray generating apparatus in order to acquire information on energy of the X-rays emitted from said X-ray generating apparatus; and
    an X-ray energy information identifying section configured to identify information on energy of the X-rays emitted from said X-ray generating apparatus based on the information detected by said second X-ray detector.

2. The X-ray CT apparatus according to claim 1, wherein said second X-ray detector is disposed at an edge of said first X-ray detector.

3. The X-ray CT apparatus according to claim 1, wherein said second X-ray detector comprises a semiconductor detector configured to count photons, and information on energy is identified based on the count of photons.

4. The X-ray CT apparatus according to claim 3, wherein said semiconductor detector configured to count photons is made by using a material selected from a group consisting of CdTe, CdZnTe, $HgI_2$, $PbI_2$ and GaAs.

5. The X-ray CT apparatus according to claim 1, wherein said second X-ray detector comprises an X-ray detector comprising scintillators and photodiodes and is provided thereabove with an X-ray filter, and the information on energy is identified based on X-rays passing through said X-ray filter.

6. The X-ray CT apparatus according to claim 1, wherein said second X-ray detector is one of a plurality of X-ray detection channels of said first X-ray detector.

7. The X-ray CT apparatus according to claim 1, wherein said first X-ray detector comprises an X-ray detector comprising scintillators and photodiodes.

8. The X-ray CT apparatus according to claim 1, wherein said second X-ray detector comprises a plurality of X-ray detection channels.

9. The X-ray CT apparatus according to claim 8, wherein said plurality of X-ray detection channels are arranged in a body axis direction of said subject.

10. The X-ray CT apparatus according to claim 1, wherein said second X-ray detector is disposed in proximity of said X-ray generating apparatus.

11. The X-ray CT apparatus according to claim 10, wherein said second X-ray detector comprises a semiconductor detector configured to count photons, and the information on energy is identified based on the count of photons.

12. The X-ray CT apparatus according to claim 11, wherein said semiconductor detector configured to count photons is made by using a material selected from a group consisting of CdTe, CdZnTe, $HgI_2$, $PbI_2$ and GaAs.

13. The X-ray CT apparatus according to claim 10, wherein said second X-ray detector comprises an X-ray detector comprising scintillators and photodiodes and is provided thereabove with an X-ray filter, and the information on energy is identified based on X-rays passing through said X-ray filter.

14. The X-ray CT apparatus according to claim 1, wherein said X-ray generating apparatus is configured to generate X-rays with a plurality of energy spectra based on a plurality of X-ray tube voltages.

15. The X-ray CT apparatus according to claim 14, wherein said X-ray generating apparatus is configured to generate the X-rays with a plurality of energy spectra by a single X-ray generating apparatus switching between a plurality of X-ray tube voltages on a view-by-view or views-by-views basis.

16. The X-ray CT apparatus according to claim 1, further comprising: a data correcting section configured to correct data based on X-rays detected by said first X-ray detector, the correction made based on the information on energy identified by said X-ray energy information identifying section.

17. The X-ray CT apparatus according to claim 1, further comprising: a display section configured to display the information on energy of the X-rays emitted from said X-ray generating apparatus.

18. An X-ray Computed Tomography (CT) apparatus comprising:
- an X-ray generating apparatus configured to generate X-rays and to emit the X-rays toward a subject;
- an X-ray filter configured to form an X-ray beam from the X-rays emitted by said X-ray generating apparatus;
- a first X-ray detector comprising a plurality of X-ray detection channels configured to detect the X-rays within the X-ray beam;
- a second X-ray detector configured to detect the X-rays within the X-ray beam in order to acquire information on energy of the X-rays;
- an X-ray energy information identifying section configured to identify information on energy of the X-rays within the X-ray beam based on the information detected by said second X-ray detector; and
- an image reconstruction section configured to generate a tomographic image based on the information on energy identified by said X-ray energy information identifying section.

19. The X-ray CT apparatus according to claim 18, wherein said second X-ray energy detector is positioned with respect to one of said X-ray filter and said first X-ray detector.

20. An X-ray Computed Tomography (CT) method comprising:
- generating X-rays and emitting the X-rays toward a subject using an X-ray generating apparatus;
- detecting the X-rays emitted by the X-ray generating apparatus using a first X-ray detector, the first X-ray detector including a plurality of X-ray detection channels;
- detecting the X-rays emitted by the X-ray generating apparatus using a second X-ray detector in order to acquire information on energy of the X-rays emitted by the X-ray generating apparatus;
- identifying information on energy of the X-rays emitted by the X-ray generating apparatus using an X-ray energy information identifying section, the information on energy identified based on the information detected by the second X-ray detector; and
- generating a tomographic image using an image reconstruction section based on the information on energy identified by the X-ray energy information identifying section.

* * * * *